US011452766B2

(12) United States Patent
Finzi et al.

(10) Patent No.: US 11,452,766 B2
(45) Date of Patent: *Sep. 27, 2022

(54) TREATMENT OF PANIC DISORDER USING BOTULINUM TOXIN

(71) Applicant: Maryland Mental Health Institute, LLC, Chevy Chase, MD (US)

(72) Inventors: Eric Finzi, Washington, DC (US); Norman E. Rosenthal, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/084,833

(22) Filed: Oct. 30, 2020

(65) Prior Publication Data

US 2021/0046167 A1 Feb. 18, 2021

Related U.S. Application Data

(63) Continuation of application No. 16/233,003, filed on Dec. 26, 2018, now Pat. No. 10,828,348, which is a continuation of application No. 15/725,178, filed on Oct. 4, 2017, now abandoned, which is a continuation of application No. 15/277,909, filed on Sep. 27, 2016, now Pat. No. 9,801,515, which is a continuation of application No. 14/984,299, filed on Dec. 30, 2015, now abandoned, which is a continuation of application No. 14/538,503, filed on Nov. 11, 2014, now Pat. No. 9,254,314.

(60) Provisional application No. 61/903,292, filed on Nov. 12, 2013.

(51) Int. Cl.
*A61K 38/48* (2006.01)
*A61K 45/06* (2006.01)
*A61K 31/5513* (2006.01)

(52) U.S. Cl.
CPC ...... *A61K 38/4893* (2013.01); *A61K 31/5513* (2013.01); *A61K 45/06* (2013.01); *C12Y 304/24069* (2013.01)

(58) Field of Classification Search
None
See application file for complete search history.

(56) References Cited

U.S. PATENT DOCUMENTS

| | | | |
|---|---|---|---|
| 7,393,537 B2 | 7/2008 | Ackerman | |
| 7,758,872 B1 | 7/2010 | Finzi | |
| 7,824,694 B2 | 11/2010 | Finzi | |
| 8,414,902 B2 | 4/2013 | Finzi | |
| 8,747,865 B2 | 6/2014 | Ackerman | |
| 8,889,151 B2 | 11/2014 | Turkel | |
| 8,926,991 B2 | 1/2015 | Borodic | |
| 9,060,964 B2 | 6/2015 | Finzi | |
| 9,078,892 B2 | 7/2015 | Turkel | |
| 9,078,893 B2 | 7/2015 | Turkel | |
| 9,254,314 B2 | 2/2016 | Finzi | |
| 9,533,029 B2 | 1/2017 | Finzi | |
| 9,555,085 B2 | 1/2017 | Turkel et al. | |
| 9,808,515 B2 | 11/2017 | Finzi et al. | |
| 9,950,045 B2 | 4/2018 | Finzi | |
| 10,751,395 B2* | 8/2020 | Finzi | A61P 25/24 |
| 10,828,348 B2* | 11/2020 | Finzi | C12Y 304/24069 |
| 2006/0083758 A1 | 4/2006 | Dadas | |
| 2007/0009555 A1 | 1/2007 | Borodic | |
| 2008/0043000 A1 | 2/2008 | Currid et al. | |
| 2010/0249036 A1 | 9/2010 | Finzi | |
| 2011/0218215 A1 | 9/2011 | Holly | |
| 2012/0021991 A1 | 1/2012 | Ackerman | |
| 2013/0189307 A1 | 7/2013 | Finzi | |
| 2014/0205590 A1 | 7/2014 | Blumenfeld | |
| 2015/0132282 A1 | 5/2015 | Finzi et al. | |
| 2015/0290302 A1 | 10/2015 | Finzi | |
| 2016/0114015 A1 | 4/2016 | Finzi et al. | |
| 2016/0166658 A1 | 6/2016 | Parashkev | |
| 2016/0256531 A1 | 9/2016 | Finzi et al. | |
| 2017/0014493 A1 | 1/2017 | Finzi et al. | |
| 2017/0100465 A1 | 4/2017 | Finzi | |
| 2017/0173123 A1 | 6/2017 | Blumenfeld | |
| 2017/0258879 A1 | 9/2017 | Finzi et al. | |
| 2019/0365873 A1* | 12/2019 | Finzi | A61K 31/5513 |
| 2021/0046167 A1* | 2/2021 | Finzi | A61K 38/4893 |

FOREIGN PATENT DOCUMENTS

| | | |
|---|---|---|
| EP | 2394645 | 12/2011 |
| WO | WO 2006/138127 | 12/2006 |
| WO | WO 2007/044809 | 4/2007 |
| WO | WO 2009/139739 | 11/2009 |
| WO | WO 2014/078724 | 5/2014 |

(Continued)

OTHER PUBLICATIONS

American Headache Society, "Meeting Info: 56th Annual Meeting of the American Headache Society," *Headache* 54:45 (Abstract Only) (2014).
Borodic et al., "Therapy with botulinum toxin," in *Neurological Disease and Therapy* (eds. Jankovic et al.) pp. 119-157 (1994).
Cardiff University News and Views, "Treating laughter lines leaves patients feeling more depressed," (Apr. 11, 2013), available on line at http://www.cardiff.ac.uk/news/view/45697-treating-laughter-lines-leaves-patients-feeling-more-depressed.
Finzi and Rosenthal, "Treatment of depression with onabotulinumtoxinA: A randomized, double-blind, placebo controlled trial," Journal of Psychiatric Research 52:1-6 (2014).

(Continued)

*Primary Examiner* — Nita M. Minnifield
(74) *Attorney, Agent, or Firm* — Klarquist Sparkman, LLP

(57) ABSTRACT

Methods are disclosed for treating social anxiety disorder, obsessive compulsive disorder, and/or panic disorder in a subject. The methods include administering a therapeutically effective amount of a neurotoxin to a corrugator supercilii and/or a procerus muscle of the subject to cause paralysis of the corrugator supercilii and/or a procerus muscle in the subject, thereby treating PTSD. The neurotoxin can be Botulinum toxin A, such as at a dose of about 20 to about 50 units of Botulinum toxin A.

10 Claims, 3 Drawing Sheets

(56) References Cited

FOREIGN PATENT DOCUMENTS

WO    WO 2015/011447    1/2015
WO    WO 2017/016880    2/2017

OTHER PUBLICATIONS

Hexsel et al., "Evaluation of self-esteem and depression symptoms in depressed and nondepressed subjects treated with onabotulinumtoxina for glabellar lines," *Dermatologic Surgery* 39(7):1088-1096 (Jul. 1, 2013).

International Search Report for PCT Application No. PCT/US2014/065029, 5 pages (dated Mar. 2, 2015).

Kim et al., "Botulinum toxin-induced facial muscle paralysis affects amygdala responses to the perception of emotional expressions: preliminary findings from an A-B-A design," *Biology of Mood & Anxiety Disorders* 4:11 (8 pages) (2014).

Wollina et al., "Managing adverse events associated with botulinum toxin type A: a focus on cosmetic procedures," *Am J Clin Dermatol* 6:141-150 (2005).

Wollmer et al., "Shrink that frown! Botulinum toxin therapy is lifting the face of psychiatry," *Giornale Italiano di Dermatologia e Venereologia* 153:540-548 (Abstract Only) (2018).

Written Opinion for PCT Application No. PCT/US2014/065029, 6 pages (dated Mar. 2, 2015).

Zuger, "Simple only on the surface," *The New York Times*, Feb. 25, 2013.

* cited by examiner

TREATMENT OF PANIC DISORDER USING BOTULINUM TOXIN

CROSS REFERENCE TO RELATED APPLICATIONS

This is a continuation of U.S. patent application Ser. No. 16/233,003 filed on Dec. 26, 2018, issued as U.S. Pat. No. 10,828,348, which is a continuation of U.S. patent application Ser. No. 15/725,178 filed on Oct. 4, 2017, now abandoned, which is a continuation of U.S. patent application Ser. No. 15/277,909, filed on Sep. 27, 2016, issued as U.S. Pat. No. 9,808,515, which is a continuation of U.S. patent application Ser. No. 14/984,299, filed on Dec. 30, 2015, now abandoned, which is a continuation of U.S. patent application Ser. No. 14/538,503, filed on Nov. 11, 2014, issued as U.S. Pat. No. 9,254,314, which claims the benefit of U.S. provisional application 61/903,292, filed on Nov. 12, 2013. The prior applications are incorporated herein by reference in their entirety.

FIELD

This disclosure relates to the field of psychiatric disorders and in particular, to methods for treating social anxiety disorder, obsessive compulsive disorder and panic disorder that utilize a neurotoxin such as botulinum toxin A.

BACKGROUND

Anxiety disorders are a group of psychological conditions whose key features include excessive anxiety, fear, worry, avoidance, and compulsive rituals, and produce or result in inordinate morbidity, overutilization of healthcare services, and functional impairment. These disorders are among the most prevalent psychiatric conditions in the United States; women are more likely than men to experience anxiety disorders. Anxiety disorders listed in the Diagnostic and Statistical Manual of Mental Disorders (4$^{th}$ Ed., The American Psychiatric Association, Washington, D.C., U.S.A., 1994, pp. 393 to 444), include panic disorder with and without agoraphobia, agoraphobia without history of panic disorder, specific phobia, social phobia, obsessive-compulsive disorder (OCD), post-traumatic stress disorder (PTSD), acute stress disorder, generalized anxiety disorder (GAD), anxiety disorder due to a general medical condition, substance-induced anxiety disorder, and specific phobias.

Panic disorder is an anxiety disorder whose essential feature is the presence of recurrent panic attacks that are discrete periods of intense fear or discomfort. The attacks usually last minutes (or, rarely, hours), are unexpected and do not, as in simple phobia, tend to occur immediately before or on exposure to a situation that almost always causes anxiety. Panic attacks typically begin with the sudden onset of intense apprehension or fear, and are accompanied by physical symptoms such as shortness of breath, dizziness, faintness, choking, palpitations, trembling, sweating, shaking, nausea, numbness, hot flushes or chills, chest pain or the like. Panic disorder may be associated with agoraphobia, in severe cases of which the person concerned is virtually housebound.

In obsessive-compulsive disorder, the primary symptom is recurrent obsessions (i.e., recurrent and intrusive thoughts, images or urges that cause marked anxiety) and/or compulsions (i.e., repetitive behaviors or mental acts that are performed to reduce the anxiety generated by one's obsessions) of sufficient severity to cause distress, be time consuming or to interfere significantly with a person's normal routine or lifestyle. Anxiety is an associated feature of this disorder: an affected person may, for example, show a phobic avoidance of situations that involve the cause of the obsession. Typical obsessions concern contamination, doubting (including self-doubt) and disturbing sexual or religious thoughts. Typical compulsions include washing, checking, ordering, and counting.

Social anxiety disorder is characterized by the persistent fear of social or performance situations in which embarrassment may occur, such as parties, meetings, eating in front of others, writing in front of others, public speaking, conversations, meeting new people, and other related situations. Exposure to social or performance situations provokes an immediate anxiety response, as well as sweating, trembling, racing or pounding heartbeat, mental confusion, and a desire to flee. Social avoidance and isolation can also become extreme, especially in the more generalized condition.

There is a need for new treatment agents to alleviate the symptoms of social anxiety disorder, obsessive compulsive disorder or a panic disorder, in order to allow subjects with these conditions to live more productive and enjoyable lives.

SUMMARY

Methods are disclosed for treating an anxiety disorder in a subject, such as social anxiety disorder, an obsessive compulsive disorder and/or a panic disorder. The methods include administering a therapeutically effective amount of a neurotoxin to a corrugator supercilii and/or a procerus muscle of the subject to cause paralysis of the corrugator supercilii and/or a procerus muscle, thereby treating the social anxiety disorder, the obsessive compulsive disorder or the panic disorder in the subject.

In some embodiments, the methods include selecting a subject with an anxiety disorder, such as a social anxiety disorder, an obsessive compulsive disorder and/or a panic disorder, and administering a therapeutically effective amount of Botulinum toxin A to a corrugator supercilii muscle and a procerus muscle of the subject, in order to cause paralysis of the corrugator superciliimuscle and procerus muscle and treat the social anxiety disorder, the obsessive compulsive disorder or the panic disorder in the subject. In some non-limiting examples, the subject does not have an underlying muscular physical condition such as torticollis or blepharospasm that is treatable with Botulinum A toxin. In other examples the Botulinum toxin A is selectively administered only to the corrugator supercilii muscle or procerus muscle or selectively only to both of these muscles. In further embodiments, the subject does not have post-traumatic stress disorder (PTSD), and/or depression and/or a mood disorder.

The foregoing and other features and advantages will become more apparent from the following detailed description of several embodiments, which proceeds with reference to the accompanying figures.

DETAILED DESCRIPTION

Figure 1:
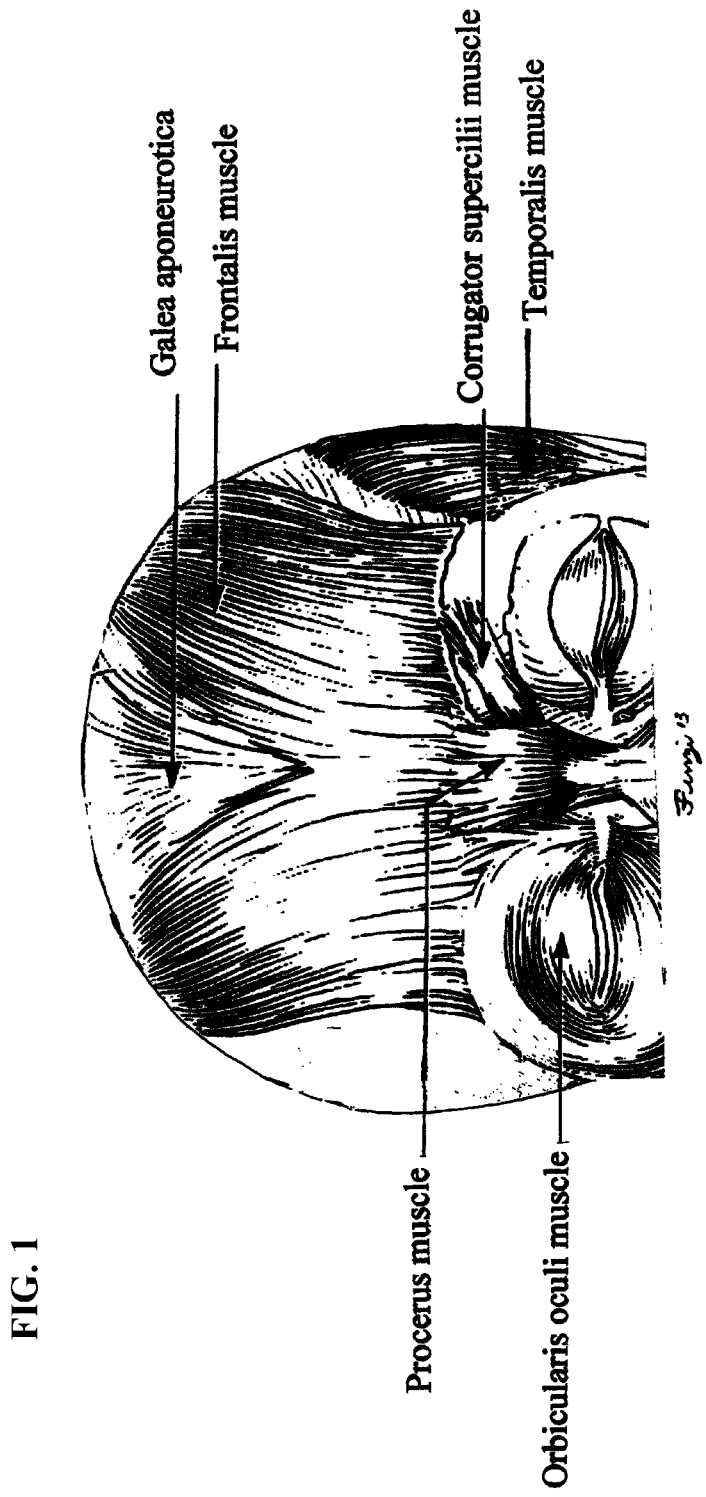
FIG. 1 is a schematic diagram of a frontal view of the musculature of the human face and neck. Injection sites for a neurotoxin, such as Botullinum Toxin (BTX) including the procerus and the corrugator supercilii are shown.

Methods are disclosed herein for treating an anxiety disorder, such as a social anxiety disorder, an obsessive compulsive disorder or a panic disorder. The subject can have a disorder including or consisting of the anxiety disorder, such as the social anxiety disorder, the obsessive compulsive disorder or the panic disorder. The methods include administering a therapeutically effective amount of a neurotoxin to the corrugator supercilii and/or the procerus muscle of the subject to cause paralysis, thereby treating the anxiety disorder, such as the social anxiety disorder, an obsessive compulsive disorder or a panic disorder in the subject.

Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Absent an underlying physical disorder: A phrase used to describe a muscular disorder (for example, torticollis) or cosmetic issue (for example, wrinkles) that is already known to be reduced or prevented by treatment with botulinum toxin that is not present in a subject. For example, the method includes selecting a subject that does not have a muscular disorder or condition, such as a subject that does not have spasms, cramping, tightness of muscles caused by medical problems, or torticollis. A physical condition can be someone that has need and/or interest in cosmetic application of Botulinum toxin, such as to decrease wrinkles. For example, the method includes selecting a subject that does not have an underlying cosmetic issue (such as wrinkles) and/or is not selected for treatment for this underlying cosmetic disorder.

Ameliorating or ameliorate: Any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation. For example, a clinical guide to monitor the effective amelioration of a psychiatric disorder, such as depression, is found in the Structured Clinical Interview for DSM-IV Axis I mood disorders ("SCID-P") (see fourth edition of *Diagnostic and Statistical Manual of Mental Disorders* (1994) Task Force on DSM-IV, American Psychiatric Association ("DSM-IV"); Kaplan, Ed. (1995); *Comprehensive Textbook of Psychiatry/VI*, vol. 1, sixth ed., pp 621-627, Williams & Wilkins, Baltimore, Md.).

Administration: To provide or give a subject an agent by any effective route. Exemplary routes of administration include, but are not limited to, oral; injection, continuous or intermittent infusion (such as subcutaneous, intramuscular, intradermal, intrathecal, epidural, intracranial, intraperitoneal, and intravenous); sublingual; rectal; transdermal; intranasal; vaginal; and inhalation routes.

Anti-Depressant Medications: A pharmaceutical agent that can be administered as a treatment for depression but are also administered for other conditions such as anxiety disorders, obsessive compulsive disorder, chronic pain, attention deficit disorder, substance abuse and sleep disorders. Anti-depressant medications include synthesized chemical compounds as well as naturally occurring or herbal remedies such as St. John's Wort. Generally, these medications are administered orally, but they may also be administered in any form of use to a medical practitioner. Examples of antidepressant medications include tricyclic antidepressants, which generally affect the two chemical neurotransmitters, norepinephrine and serotonin. Tricyclics include imipramine, amitriptyline, nortriptyline, and desipramine. Monoamine oxidase inhibitors (MAOIs) are also used as antidepressants. MAOIs approved for the treatment of depression include phenelzine (Nardil), tranylcypromine (Parnate), and isocarboxazid (Marplan). Medications that primarily affect the neurotransmitter serotonin, termed selective serotonin reuptake inhibitors (SSRIs), are also used as antidepressants. These include escitalopram HBr (Lexapro), fluoxetine (Prozac), sertraline (Zoloft), fluvoxamine (Luvox), paroxetine (Paxil), and citalopram (Celexa). Additional medications of use affect both norepinephrine and serotonin (SNRIs), for example venlafaxine (Effexor) and nefazadone (Serzone), or atypical agents such as mirtazepine (Remeron), nefazodone (Serzone), triazolopyridine (trazodone), and bupropion (Wellbutrin).

Anxiety disorder: Anxiety disorders include disorders that share features of excessive fear and anxiety related behavioral disturbances. Fear is the emotional response to real or perceived imminent threat, whereas anxiety is anticipation of future threat. These two states overlap but differ. Fear is more often associated with surges of autonomic arousal necessary for fight or flight, thoughts of immediate danger, and escape behaviors, while anxiety is more often associated with muscle tension and vigilance in preparation for future danger and cautious or avoidant behaviors. Sometimes the level of fear or anxiety is reduced by pervasive avoidance behaviors. Panic attacks feature prominently within the anxiety disorders as a particular type of fear response. Panic attacks are not limited to anxiety disorders but rather can be seen in other mental disorders as well.

The anxiety disorders differ from one another in the types of objects or situations that induce fear, anxiety, or avoidance behavior, and the associated cognitive ideation. Thus, while the anxiety disorders tend to be highly comorbid with each other, they can be differentiated by close examination of the types of situations that are feared or avoided and the content of the associated thoughts or beliefs. Anxiety disorders include generalized anxiety disorder, phobias, panic disorder, agoraphobia, social anxiety disorder, obsessive-compulsive disorder, separation anxiety, and situation anxiety.

Benzodiazepine: A group of psychoactive medications whose core chemical structure is the fusion of a benzene ring and a diazepine ring, that are used for treating panic disorder, insomnia, and generalized anxiety disorder, amongst other indications. Benzodiazepines include, but are not limited to, 2-keto compounds (such as chlordiazepoxide, clorazepae, diazepam, flurazepam, halazepam, and prazepam), 3-hydroxy compounds (such as lorazepam, lormetazepam, oxazepam, and temazepam), 7-nitro compounds (such as clonazepam, flunitrazepam, nimetazepam, and nitrazepam), Triazolo compounds (such as adinazolam, alprazolam, estazolam, triazolam, and imidazo compounds (such as climazolam, loprazolam, and midazolam).

Beta Blocker: A beta-adrenergic antagonist that is a drug that targets the beta adrenergic receptor to block the action of endogenous catecholamines.

Blood Brain Barrier: A separation of circulating blood from the brain extracellular fluid (BECF) in the central nervous system (CNS). It occurs along all capillaries and is composed of tight junctions around the capillaries that do not exist in the general circulation. This barrier also includes a thick basement membrane and astrocytic endfeet. This barrier restricts the diffusion of microscopic objects (such as bacteria) and other molecules, such as toxins, large molecules, and/or hydrophilic molecules into the cerebrospinal fluid (CSF), while allowing the diffusion of small hydrophobic molecules ($O_2$, $CO_2$, hormones). Cells of the barrier actively transport metabolic products such as glucose across the barrier with specific proteins.

Depressive Disorder: A mood disorder characterized by a predominantly sad or depressed mood, typically but not always of two or more weeks' duration. A depressive disorder also has other signs or symptoms accompanying a sad or depressed mood, including one or more of: decreased energy, appetite changes, weight gain or loss, insomnia or hypersomnia, recurrent thoughts or death, thoughts of suicide, loss of interest in usual activities, slowed thinking or cognitive speed, increased speech latency, decreased volume of speech, excessive or inappropriate guilt, diminished concentration, feeling sluggish, and slower than normal motor activity (such as gross motor, fine motor, speech). Depressive disorders can be accompanied by perceptual disturbances. Depressive disorders can be caused by a medical disorder (e.g., endocrine disorders, lupus), medication side-effect (e.g., interferon), substance use disorder, neurologic disorder (e.g., seizure disorder, traumatic brain injury), or have no clear cause.

Botulinum toxin: A toxin produced by the bacterium *Clostridium botulinum*, but which may either be obtained from a natural source or made by synthetic means. Seven immunologically distinct Botulinum neurotoxins have been characterized, these being respectively Botulinum neurotoxin serotypes A, B, $C_1$, D, E, F and G, each of which is distinguished by neutralization with type-specific antibodies. The different serotypes of Botulinum toxin vary in the animal species that they affect and in the severity and duration of the paralysis they evoke. For example, it has been determined that Botulinum toxin type A is 500 times more potent, as measured by the rate of paralysis produced in the rat, than is Botulinum toxin type B. Additionally, Botulinum toxin type B has been determined to be non-toxic in primates at a dose of 480 U/kg which is about 12 times the primate $LD_{50}$ for Botulinum toxin type A (Moyer et al., "Botulinum Toxin Type B: Experimental and Clinical Experience," in *Therapy With Botulinum* Toxin, Marcel Dekker, Inc. Jankovic et al. (eds.), pgs. 71-85, 1994).

Depression: A mental state of depressed mood characterized by feelings of sadness, despair and discouragement. Depression includes feelings of sadness considered to be normal (mild depression), dysthymia, and major depression. Depression can resemble the grief and mourning that follows bereavement, and there are often feelings of low self esteem, guilt and self reproach, withdrawal from interpersonal contact and somatic symptoms such as alterations in eating habits and sleep disturbances.

Frown: To furrow the brow to show unhappiness or displeasure. This action uses the orbicularis oculi, the frontalis muscle and/or the corrugator supercilii muscle. This action can also include the use of the procerus muscle.

Hallucination: Altered, misperceived, or incorrect sensory experiences. See "perceptual disturbances" below for additional information.

Mood: A person's subjective report on their emotional perspective on self, situation, future, or past. While mood can fluctuate from states such as "happy," "sad," "angry," or "pleased" within a day, a prolonged state of sad or depressed mood is a defining characteristic of a depressive illness.

Mood disorder: A medical, neurologic, or psychiatric disorder with the primary sign or symptom as an alteration in mood. Mood disorders are usually classified as depressive (e.g., principal mood symptom is a sustained sad or depressed mood) or manic (e.g., principal mood symptom is a sustained expansive, elevated, or irritable mood). Symptoms or signs beyond the mood state proper may be required to diagnose a mood disorder.

Nightmare: A frightening dream that causes the interruption of sleep. Repeated instances of nightmares can lead to a specific sleep disorder diagnosis of Nightmare Disorder. Nightmares are also commonly observed as a symptom in PTSD and other anxiety conditions.

Obsessive Compulsive Disorder: A pervasive pattern of preoccupation with orderliness, perfectionism, and mental interpersonal control, at the expense of flexibility, openness, and efficiency, beginning by early adulthood and present in a variety of contexts, as indicated by four (or more) of the following:

1. Is preoccupied with details, rules, lists, order, organization, or schedules to the extent that the major point of the activity is lost.

2. Shows perfectionism that interferes with task completion.

3. Is excessively devoted to work and productivity to the exclusion of leisure activities and friendships (not accounted for by obvious economic necessity).

4. Is overconscientious, scrupulous, and inflexible about matters of morality, ethics or values.

5. Is unable to discard worn-out or worthless objects even when they have no sentimental value.

6. Is reluctant to delegate tasks or to work with others unless they submit to exactly his or her way of doing things.

7. Adopts a miserly spending style towards both self and others; money is viewed as something to be hoarded for future catastrophes.

8. Shows rigidity and stubbornness.

Thus, obsessive compulsive disorder can be characterized by at least 4, 5, 6, 7 or all 8 of these characteristics.

Panic Attack: An abrupt surge of intense fear or intense discomfort, that can occur from a calm state or an anxious state, that reaches a peak within minutes, and during which four (or more) of the following symptoms occur:

1. Palpitations, pounding heart, or accelerated heart rate.
2. Sweating.
3. Trembling or shaking.
4. Sensations of shortness of breath or smothering.
5. Feelings of choking.
6. Chest pain or discomfort.
7. Nausea or abdominal distress.

8. Feeling dizzy, unsteady, light-headed, or faint.
9. Chills or heat sensations.
10. Paresthesias (numbness or tingling sensations).
11. Derealization (feelings of unreality) or depersonalization (being detached from one-self).
12. Fear of losing control or "going crazy."
13. Fear of dying.

Thus, at least 4, 5, 6, 7, 8, 9, 10, 11 or 12 of these symptoms can occur during a panic attack.

Panic Disorder: Recurrent unexpected panic attacks (see Criterion A, below). A panic attack is an abrupt surge of intense fear or intense discomfort that reaches a peak within minutes, and during which time four or more of a list of 13 physical and cognitive symptoms occur. The term recurrent means more than one unexpected panic attack. The term unexpected refers to a panic attack for which there is no obvious cue or trigger at the time of occurrence so that the attack appears to occur without warning, such as when the individual is relaxing or emerging from sleep (nocturnal panic attack). In contrast, expected panic attacks are attacks for which there is an obvious cue or trigger, such as a situation in which panic attacks typically occur. The determination of whether panic attacks are expected or unexpected is made by the clinician. Approximately one-half of individuals with panic disorder have expected panic attacks as well as unexpected panic attacks, so that the presence of expected panic attacks does not rule out the diagnosis of panic disorder. The frequency and severity of panic attacks vary widely. In terms of frequency, there may be moderately frequent attacks (such as one per week or per ten days) for months at a time, or short bursts of more frequent attacks (such as daily or twice daily) separated by weeks or months without any attacks or with less frequent attacks (such as two per month) over many years. In terms of severity, individuals with panic disorder may have both full-symptom (four or more symptoms) and limited-symptom (fewer than four symptoms) attacks, and the number and type of panic attack symptoms frequently differ from one panic attack to the next. However, more than one unexpected full-symptom panic attack is required for the diagnosis of panic disorder.

The worries about panic attacks or their consequences usually pertain to physical concerns, such as worry that panic attacks reflect the presence of life-threatening illnesses (e.g., cardiac disease, seizure disorder); social concerns, such as embarrassment or fear of being judged negatively by others because of visible panic symptoms; and concerns about mental functioning, such as "going crazy" or losing control (Criterion B, see below). A panic disorder is characterized by the following features:

A. Recurrent unexpected panic attacks.
B. At least one of the attacks has been followed by 1 month (or more) of one or both of the following:
  1. Persistent concern or worry about additional panic attacks or their consequences; and
  2. A significant maladaptive change in behavior related to the attacks (such as, but not limited to, behaviors designed to avoid having the panic attacks).
C. The disturbance is not attributable to the physiological effects of a substance (for example, a drug of abuse, a medication) or another medical condition (such as, but not limited to, hyperthyroidism or cardiopulmonary disorders).
D. The disturbance is not better explained by another mental disorder, such as a social anxiety disorder; a specific phobia; obsessive-compulsive disorder; posttraumatic stress disorder; or separation anxiety disorder.

Perceptual disturbance: An altered perception or conscious experience of sensory information. A common perceptual disturbance is a hallucination (incorrect perception of auditory, visual, tactile, olfactory, or gustatory sense information). Another common perceptual disturbance is a flashback (the sensory experience of being in a different place and/or time, often in response to a sensory trigger (e.g., after hearing a car backfire, a combat veteran has a momentary sensation of being back at war)). Altered reality testing is sometimes used to describe a person experiencing perceptual disturbances because the person is not accurately perceiving sensory stimuli.

Post-Traumatic Stress Disorder (PTSD): A disorder that can occur after experiencing a traumatic event that leaves a subject feeling scared, confused, and/or angry to the extent that daily activities are difficult to perform. A traumatic event can include combat or military exposure, child sexual or physical abuse, terrorist attacks, sexual or physical assault, serious accidents, and natural disasters (such as a fire, tornado, hurricane, flood, or earthquake). PTSD is defined by the Diagnostic and Statistical Manual (DSM), Fourth-Edition, Text Revision, published by the American Psychiatric Associating (DSM-IV-TR), and the DSM-V.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. In addition to biologically-neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate.

Psychiatric disorder: Any disorder that results in altered or abnormal behavior, function, or subjective distress in one or more of the following intrapersonal or interpersonal realms: mood, anxiety, memory, cognition, consciousness, perception, sexual experience, sleep, substance use/addiction, personality, attention/concentration, psychosis, identity, eating, or bodily function or integrity. A psychiatric disorder typically causes the patient or others around the patient noticing social, interpersonal, and/or occupational distress or dysfunction. The cause (etiology) of a psychiatric disorder may be idiopathic (unknown), or it may be due to a recognized psychosocial stressor, a medical disorder, or a neurological disorder.

Psychotic: A psychiatric condition in its broadest sense, as defined in the DSM-IV (Kaplan, ed. (1995) supra). Different disorders which have a psychotic component comprise different aspects of this definition of "psychotic." For example, in schizophreniform disorder, schizoaffective disorder and brief psychotic disorder, the term "psychotic" refers to delusions, any prominent hallucinations, disorganized speech, or disorganized or catatonic behavior. In psychotic disorder due to a general medical condition and in substance-induced psychotic disorder, "psychotic" refers to delusions or only those hallucinations that are not accompanied by insight. Finally, in delusional disorder and shared psychotic disorder, "psychotic" is equivalent to "delusional" (see DSM-IV, supra, page 273).

Objective tests can be used to determine whether an individual is psychotic and to measure and assess the success of a particular treatment schedule or regimen. For example, measuring changes in cognitive ability aids in the diagnosis and treatment assessment of the psychotic patient.

Any test known in the art can be used, such as the so-called "Wallach Test," which assesses recognition memory (see below, Wallach, *J. Gerontol.* 35:371-375, 1980). Another example of an objective text that can be used to determine whether an individual is psychotic and to measure efficacy of an anti-psychotic treatment is the Stroop Color and Word Test ("Stroop Test") (see Golden, C. J., Cat. No. 30150M, in *A Manual for Clinical and Experimental Uses*, Stoelting, Wood Dale, Ill.). The Stroop Test is an objective neuropsychiatric test that can differentiate between individuals with psychosis and those without.

Psychosis: A psychiatric symptom, condition or syndrome in its broadest sense, as defined in the DSM-IV (Kaplan, ed. (1995) supra), comprising a "psychotic" component, as broadly defined above. Psychosis is typically defined as a mental disorder or condition causing gross distortion or disorganization of a person's mental capacity, affective response, and capacity to recognize reality, communicate, and relate to others to the degree of interfering with his capacity to cope with the ordinary demands of everyday life.

Psychotic major depression: A condition also referred to as psychotic depression (Schatzberg, *Am. J. Psychiatry* 149:733-745, 1992), "psychotic (delusional) depression," "delusional depression," and "major depression with psychotic features" (see the DSM-III-R). This condition is a distinct psychiatric disorder that includes both depressive and psychotic features. Individuals manifesting both depression and psychosis, i.e. psychotic depression, are often referred to as "psychotic depressives."

Seizure Disorder: A "paroxysmal event due to abnormal, excessive, hypersynchronous discharges from an aggregate of central nervous system (CNS) neurons" that may or may not result in observable changes in behavior (Chapter 363 of *Harrison's Principles of Internal Medicine* (Fauci A S, Kasper D L, et al. (editors), $17^{th}$ Edition, 2008). A seizure is a single event while epilepsy or seizure disorder is a medical diagnosis to describe a condition characterized by repeated seizures. Various types of seizures include simple partial, complex partial, partial with secondary generalization, absence, atypical absence, generalized tonic-clonic, atonic, myoclonic, or unclassified. Brain injury as defined above is a recognized cause of seizures. Seizures can be associated with various additional clinical problems: cognitive changes, mood or anxiety changes, interictal behavior changes, sudden death, psychosocial impairments, occupational problems, or psychosis.

Scowl: A facial expression showing displeasure. Scowling primarily utilizes the corrugator supercilii muscle and the procerus muscle.

Selective Serotonin Reuptake Inhibitor (SSRI): A type of antidepressant medication that is prescribed for the treatment of various psychiatric conditions, including, but not limited to, a depressive disorder or an anxiety disorder. Commonly prescribed SSRIs include fluoxetine, paroxetine, sertraline, citalopram, escitalopram, and fluvoxamine. Other non-limiting examples of SSRI include prodrug or pharmacologically active metabolite of these SSRI medications.

Sertraline: A selective serotonin reuptake inhibitor that is prescribed to treat one or more of the following indications: major depression or a depressive disorder, OCD, PTSD, panic disorder, social phobia, PMDD, or an anxiety disorder.

Sign: An observation, result, finding, or outcome on a medical test or examination that may indicate the presence of an associated medical, neurologic, or psychiatric condition. Non-limiting examples include observed behavior reported by a non-medical observer (e.g., family member, friend, law enforcement officer, clergy, fellow member of a military unit); observed behaviors during clinical evaluation such as anxiety noted on mental status examination; psychological or neuropsychological test results; laboratory value from blood, urine, cerebrospinal fluid; radiologic examinations such as x-rays, CT or MR scans; physical examination results such as impaired coordination or disconjugate eye movements on neurological examination, or elevated blood pressure on physical examination; or oculomotor function on vestibulo-oculomotor examination.

Sleep disorder: A disorder of sleep that includes, but is not limited to, insomnia, disorders of daytime somnolence, parasomnias, chronobiological disorders, and sleep consequences of neurological disorders. Non-limiting examples of sleep disorders include rapid eye movement behavior disorder, restless legs syndrome, periodic leg movements of sleep, obstructive sleep apnea, central sleep apnea, nightmares, sleep terrors, sleepwalking, confusional arousals, sleep paralysis, sleep eating disorder, or narcolepsy (See, for example, CG Goetz (editor), *Textbook of Clinical Neurology*, $3^{rd}$ Edition, 2007, Chapter 54)

Sleep disturbance: An observed or reported alteration in the initiation, maintenance, or quality of sleep that may be a symptom or sign of a medical, neurological, or psychiatric disorder. A sleep disturbance also may be a symptom or sign of a sleep disorder.

Sleep Terrors: An awakening from sleep characterized by intense anxiety upon awakening. Sleep terrors can be differentiated from nightmares because there is significantly less recall of frightening dream content in sleep terrors. Sleep terrors may be present as a sign or symptom of another psychiatric disorder. Sleep terrors can be difficult to distinguish from nocturnal panic attacks.

Social Anxiety Disorder (SAD): According to the Diagnostic and Statistical Manual of Mental Disorders ($5^{th}$ Ed., American Psychiatric Association, Arlington, Va., 2013), a social anxiety disorder is characterized by:

A. Marked fear or anxiety about one or more social situations in which the individual is exposed to possible scrutiny by others. Examples include social interactions (e.g., having a conversation, meeting unfamiliar people), being observed (such as eating or drinking), and performing in front of others (such as giving a speech). In children, the anxiety must occur in peer settings and not just during interactions with adults.

B. The individual fears that he or she will act in a way or show anxiety symptoms that will be negatively evaluated (i.e., will be humiliating or embarrassing; will lead to rejection or offend others).

C. The social situations almost always provoke fear or anxiety. In children, the fear or anxiety may be expressed by crying, tantrums, freezing, clinging, shrinking, or failing to speak in social situations.

D. The social situations are avoided or endured with intense fear or anxiety.

E. The fear or anxiety is out of proportion to the actual threat posed by the social situation and to the sociocultural context.

F. The fear, anxiety or avoidance is persistent, typically lasting for six months or more.

G. The fear, anxiety or avoidance causes clinically significant distress or impairment in social, occupational, or other important areas of functioning.

H. The fear, anxiety or avoidance is not attributable to the physiological effects of a substance (e.g., a drug of abuse, a medication) or another medical condition.

I. The fear, anxiety or avoidance is not better explained by the symptoms of another mental disorder, such as panic disorder, body dysmorphic disorder, or autism spectrum disorder.

J. If another medical condition (e.g., Parkinson's disease, obesity, disfigurement from burns or injury) is present, the fear, anxiety, or avoidance is clearly unrelated or is excessive.

Subject: Any mammal. In one embodiment, a subject is a human subject.

Symptom: A problem, complaint, or issue reported by a subject that is primarily a subjective complaint. Pain, fatigue, or changes in mood are commonly reported symptoms. Symptoms are distinguished from signs in that signs typically can be confirmed with objective evidence such as observation, tests or examinations, whereas symptoms rely upon the subject's self-report.

Therapeutically effective amount: A quantity of treatment, such as drug, for example a neurotoxin such as Botulinum toxin A, sufficient to achieve a desired effect in a subject being treated. For instance, this can be the amount of Botulinum toxin A necessary to impair contraction of, or paralyze, a facial muscle. This can also be the amount of a therapy, such as light therapy or psychotherapy, sufficient to relieve a symptom of a disorder, such as depression. This can also be the amount of an antidepressant sufficient to alter the mood of a subject.

Unit equivalents: An amount of Botulinum Toxin (BTX) that is equivalent to standard Units of Botulinum Toxin A (BTX-A). A standard Unit of BTX-A is defined as the mean $LD_{50}$ for female Swiss Webster mice weighing 18-20 grams (Schantz and Kaultner, *J. Assoc. Anal. Chem.* 61: 96-99, 1978). The estimated human $LD_{50}$ for a 70-kg person is 40 Units/kg or about 2500-3000 Units.

BOTOX™ (Botulinum toxin A, Allergan, Inc., Irvine, Calif., U.S.A.) is sold in 100 Unit vials. DYSPOR™ (Speywood Pharmaceuticals, Ltd., Maidenhead, U.K.) is sold in 300 or 500 Unit vials. For cosmetic uses, the vial contents are typically diluted with 1 or 2 ml of sterile saline solution, which for BOTOX™ provides a 100 or 50 Unit/ml dilution. DYSPORT™ BTX-A is roughly three fold less toxic than BOTOX™ and approximately three-fold greater amounts of the DYSPOR™ product will usually be injected to achieve the same result as would be obtained using a specific number of Units of BOTOX™.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Botulinum Toxin

Botulinum toxin (BTX), produced by the bacterium *Clostridium botulinum* reversibly paralyzes striated muscle when administered in sub-lethal doses. BTX has been used in the treatment in a number of neuromuscular disorders and conditions involving muscular spasm including, but not limited to, dystonia, hemifacial spasm, tremor, spasticity (e.g. resulting from multiple sclerosis), anal fissures and various ophthalmologic conditions (for example, see Carruthers et al., *J. Amer. Acad. Derm.* 34:788-797, 1996). A Botulinum toxin type A complex has been approved by the U.S. Food and Drug Administration for the treatment of blepharospasm, strabismus and hemifacial spasm.

BTX is a generic term covering a family of toxins produced by *C. botulinum* comprising up to eight serologically distinct forms (A, B, $C_1$, $C_2$, D, E, F and G). These toxins are among the most powerful neuroparalytic agents known (c.f. Melling et al., *Eye* 2:16-23, 1988). Serotypes A, B and F are the most potent. Without being bound by theory, the mode of action is believed to be an inhibition of the release of acetylcholine by the presynaptic nerve.

Botulinum toxin type A can be obtained by establishing and growing cultures of *Clostridium botulinum* in a fermenter and then harvesting and purifying the fermented mixture in accordance with known procedures. Alternatively, the Botulinum toxin serotypes are initially synthesized as inactive single chain proteins which must be cleaved or nicked by proteases to become neuroactive. High quality crystalline Botulinum toxin type A can be produced from the Hall A strain of *Clostridium botulinum*. The Schantz process can be used to obtain crystalline Botulinum toxin type A (see Schantz et al., Microbiol Rev. 56:80-99, 1992). Generally, the Botulinum toxin type A complex can be isolated and purified from an anaerobic fermentation by cultivating *Clostridium botulinum* type A in a suitable medium. This process can be used, upon separation out of the non-toxin proteins, to obtain pure Botulinum toxins, such as for example: purified Botulinum toxin type A with an approximately 150 kD molecular weight, purified Botulinum toxin type B with an approximately 156 kD molecular weight and purified Botulinum toxin type F with an approximately 155 kD molecular weight.

Botulinum toxins and/or Botulinum toxin complexes can be obtained from List Biological Laboratories, Inc., Campbell, Calif.; the Centre for Applied Microbiology and Research, Porton Down, U.K.; Wako, Osaka, Japan; Metabiologics, Madison, Wis.) as well as from Sigma Chemicals, St Louis, Mo. There are several formulations that have been approved by the U.S. Food and Drug administration, and any of these can be used in any of the methods disclosed herein. These include BOTOX®, DYSPORT®, XEOMIN®, and MYOBLOC®.

The initial cosmetic use of BTX was for treatment of forehead frown lines as reported in Carruthers and Carruthers, *J. Dermatol. Surg. Oncol.* 18:17-21, 1992. The clinical effects of peripheral intramuscular Botulinum toxin type A are usually seen within one week of injection. The typical duration of symptomatic relief from a single intramuscular injection of Botulinum toxin type A averages about three months. BTX-A serotype is available commercially for pharmaceutical use under the trademarks BOTOX™ (Allergan, Inc., Irvine, Calif., U.S.A.) and DYSPORT™ (Speywood Pharmaceuticals, Ltd., Maidenhead, U. K.). BOTOX™ consists of a purified Botulinum toxin type A complex, albumin and sodium chloride packaged in sterile, vacuum-dried form. Specifically, each vial of BOTOX™ contains about 100 Units (U) of *Clostridium botulinum* toxin type A purified neurotoxin complex, 0.5 milligrams of human serum albumin and 0.9 milligrams of sodium chloride in a sterile, vacuum-dried form without a preservative.

The Botulinum toxin type A is made from a culture of the Hall strain of *Clostridium botulinum* grown in a medium containing N-Z amine and yeast extract. The Botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C.

BOTOX™ is sold in 100 Unit vials. DYSPORT™ is sold in 300 or 500 Unit vials. BTX-A is roughly three-fold less toxic than BOTOX™ and approximately three-fold greater amounts of the DYSPORT™ product will usually be injected to achieve the same result as would be obtained using a specific number of Units of BOTOX™.

For cosmetic uses, the vial contents are typically diluted with 1 or 2 ml of sterile saline solution, which for BOTOX™ provides a 100 or 50 Unit/ml dilution. (DYSPORT™ can also be utilized.) For example, BOTOX™ can be reconstituted with sterile, non-preserved saline prior to intramuscular injection. To reconstitute vacuum-dried BOTOX™, sterile normal saline without a preservative (0.9% Sodium Chloride Injection) is used by drawing up the proper amount of diluent in the appropriate size syringe. Since BOTOX™ may be denatured by bubbling or similar violent agitation, the diluent is gently injected into the vial. For sterility reasons BOTOX™ is preferably administered within four hours after the vial is removed from the freezer and reconstituted. During these four hours, reconstituted BOTOX™ can be stored in a refrigerator at about 2° C. to about 8° C. Reconstituted, refrigerated BOTOX™ has been reported to retain its potency for at least about two weeks (see Neurology, 48:249-53:1997).

Methods for Treatment of Social Anxiety Disorder, Obsessive Compulsive Disorder and Panic Disorder Methods are provided herein for treating a social anxiety disorder, an obsessive compulsive disorder and/or a panic disorder in a subject. The methods include administering a therapeutically effective amount of a neurotoxin to a facial muscle involved in frowning, scowling, or a sad appearance. The agent causes partial or complete paralysis of the facial muscle, thereby affecting the ability of the subject to frown and thereby treat the social anxiety disorder, the obsessive compulsive disorder or the panic disorder.

The injection sites for treatment include the procerus muscle and/or the corrugator supercilii muscle. In some embodiments a therapeutically effective amount of BTX, such as BTX A, is administered to the procerus muscle and the corrugator supercilii muscle. In some embodiments, BTX is not injected into the orbicularis oculi, frontalis, and/or the depressor anguli oris muscles (triangularis muscle). In other embodiments, BTX is injected into the depressor anguli oris muscles (triangularis muscle). In yet other embodiments, the BTX does not cross the blood brain barrier.

The method involves identifying or selecting a subject who has the social anxiety disorder, the obsessive compulsive disorder and/or the panic disorder and administering the treatment to this subject. The subject can be female or male.

Anxiety disorders differ from developmentally normative fear or anxiety by being excessive or persisting beyond developmentally appropriate periods. They differ from transient fear or anxiety, often stress induced, by being persistent (e.g., typically lasting 6 months or more), although the criterion for duration is intended as a general guide with allowance for some degree of flexibility and is sometimes of shorter duration in children (as in separation anxiety disorder and selective mutism). Since individuals with anxiety disorders typically overestimate the danger in situations they fear or avoid, the primary determination of whether the fear or anxiety is excessive or out of proportion is made by the diagnostic clinician, taking cultural contextual factors into account. Many of the anxiety disorders develop in childhood and tend to persist if not treated. Most occur more frequently in females than in males (approximately 2:1 ratio). Each anxiety disorder is diagnosed only when the symptoms are not attributable to the physiological effects of a substance/medication or to another medical condition.

A subject can be selected that has the social anxiety disorder, the obsessive compulsive disorder or the panic disorder as defined by the DSM-5 criteria. A subject can also be selected that has the social anxiety disorder, the obsessive compulsive disorder or the panic disorder as defined by the DSM-IV-TR criteria.

Generally, a subject is selected that has been diagnosed with the social anxiety disorder, the obsessive compulsive disorder or the panic disorder. In some embodiments, the subject does not have an underlying physical condition that is being treated by BTX, such as a musculoskeletal condition, such as torticollis, blepharospasm, or other disorder of muscular contractions. In other embodiments, the subject does not have a muscular disorder or condition. In some examples, the subject does not have spasms, cramping, and/or tightness of muscles cause by musculoskeletal conditions/disease. In yet other embodiments, the subject does not have torticollis or blepharospasm. In additional embodiments, the subject has (or does not have) wrinkles, and is not being treated using Botulinum toxin for any cosmetic purposes, including the treatment of wrinkles. In some embodiments, the subject has a comorbid condition. In further embodiments, the subject does not have another psychiatric disorder.

In additional embodiments, the subject does not have an anxiety disorder other than the social anxiety disorder, the obsessive compulsive disorder or the panic disorder, such as post-traumatic stress disorder or a generalized anxiety disorder. In further embodiments, the subject does not have depression, such as major depression or a mood disorder. Thus, in some embodiments, the social anxiety disorder, the obsessive compulsive disorder and/or the panic disorder is/are the sole psychological disorder; the subject does not have, for example schizophrenia, depression, other anxiety disorders, and/or post-traumatic stress disorder. In some embodiments, the subject does not have a psychotic disorder. In additional embodiments, the subject does not have a sleep disorder, sleep terrors or a sleep disturbance. In further examples, the subject does not have posttraumatic stress disorder.

In additional embodiments, the methods disclosed herein are utilized concurrently with cognitive behavioral therapy and/or psychotherapy and/or electroconvulsive therapy. In particular examples, the behavioral therapy and/or psychotherapy is for treatment of a social anxiety disorder, obsessive compulsive disorder, or panic disorder. In additional embodiments, BTX, such as BTX A, is administered in conjunction with other agents.

In some embodiments, for the treatment of obsessive compulsive disorder, a therapeutically effective amount of another agent can be administered to the subject. The agent can be a therapeutically effective amount of a selective serotonin reuptake inhibitor (SSRI) such as, but not limited to, paroxetine, sertraline, fluoxetine, escitalopram and fluvoxamine, a tricyclic antidepressant, such as clomipramine. In additional embodiments, the subject is administered a benzodiazepine. In yet other embodiments, the subject is administered an atypical antipsychotic, such as olanzapine, quetiapine, and risperidone.

In additional embodiments, for the treatment of a panic disorder the subject is administered a therapeutically effective amount of an antidepressant, such as an SSRI, a monoamine oxidase inhibitor (MAOI), a tricyclic antidepressant or a norepinephrine reuptake inhibitor. The subject can be administered an anti-anxiety drug, such as a benzodiazepine. Benzodiazepines include 2-keto compounds (such as chlordiazepoxide, clonazepam, diazepam, flurazepam, alprazolam, halazepam, and prazepam), 3-hydroxy compounds (such as lorazepam, lormetazepam, oxazepam, and temazepam), 7-nitro compounds (such as clonazepam, flunitrazepam, nimetazepam, and nitrazepam), Triazolo compounds (such as adinazolam, alprazolam, estazolam, triazolam, and imidazo compounds (such as climazolam, loprazolam, and midazolam).

In yet other embodiments, for the treatment of a social anxiety disorder, the subject is administered a therapeutically effective amount of an antidepressant, such as an SSRI or a MAOI. In further embodiments, the subject is administered a therapeutically effective amount of a benzodiazepine. In additional embodiments, the subject is administered a therapeutically effective amount of a serotonin-norepinephrine reuptake inhibitors (SNRIs), such as venlafaxine, milnacipran, or mirtazapine bupropion. In yet other embodiments, the subject is administered a therapeutically effective amount of a beta-blocker, such as propranalol.

In other embodiments, the subject is administered additional medication, including, but not limited to SSRIs, such as citalopram, escitalopram, fluoxetine, fluvoxamine, paroxetine, and sertraline, and/or MAOIs. In further embodiments, Botulinum toxin is administered in conjunction with an alpha-adrenergic antagonist, such as clonidine, an anti-convulsant or mood stabilizers (for example, carbamazepine (TERGRETOL®), Topiramate (TOPAMAX®), Zolpidem (AMBIEN®)), Lamotrigine (LAMICTAL®), Valproic acid (DEPAKENE®), lithium carbonate, buspirone (BUSPAR®), and alpha adrenergic blockers such as Prazosin (MINIPRESS®). In additional embodiments, Botulinum toxin is administered with an antipsycholic agent, such as risperidone, or an atypical antidepressant, a beta blocker (such as propanolol), a benzodiazepine, a glucocorticoid (such as cortiosterone), a heterocyclic antidepressant, such as amitriptyline, or imipramine, or a MAOI, such as phenelzine.

The BTX, such as BTX A, can be administered simultaneously or sequentially with the additional modality of treatment. In one embodiment, a therapeutically effective amount of BTX, such as BTX A, is administered in combination with at least one additional modality of treatment. Useful modalities are listed above. The modality of treatment can also be physical, such as electroconvulsive therapy or light therapy. The modality can also be psychotherapy, exercise or meditation. A single modality of treatment can be combined with the BTX treatment, or a combination of additional modalities can be used with the BTX treatment.

Thus, in one example, a subject taking a therapeutically effective amount of an antidepressant medication (such as an SSRI) for the condition being treated, or undergoing a therapeutic protocol, can be treated with BTX, such as BTX A, during the course of the additional treatment. The subject can be administered an additional therapeutic agent, such as a therapeutically effective amount of one or more of a SSRI, an alpha adrenergic antagonist, an anti-convulsant, a mood stabilizer, an anti-psychotic agent, a beta blocker, a benzodiazepine, a glucocorticoid, a monamine-oxidase inhibitor (MAOIs), a heterocyclic anti-depressant, a tricyclic anti-depressant and/or an atypical anti-depressant.

BTX, such as BTX A, can be administered after the treatment with the additional agent has been terminated, or prior to the initiation of therapy, such as the administration of the antidepressant medication, psychotherapy, or a physical treatment protocol. Thus, the treatment can be simultaneous. In other embodiments, BTX is administered in the absence of treatment with these agents.

Without being bound by theory, decreased movement of muscles that are involved in the neural circuit for social anxiety disorder, the obsessive compulsive disorder or the panic disorder lessen the symptoms of the disorder. Denervation of the frown muscles results in a decreased ability of the treated subject to frown, and thus inhibits fear, anger and sadness, contributing to a subjective sense of less anxiety and/or preventing triggering of the memory. Improvement can be objectively assessed by the DSM-IV or DMSV-5 criteria, or by standardized tests known in the art. As noted above, the social anxiety disorder, the obsessive compulsive disorder or the panic disorder can be assessed. A very straightforward test is to ask the subject to report whether the intensity of the symptoms are altered by treatment with BTX, such as BTX A.

For example the present methods can result in a decrease in panic attacks, either in intensity or frequency, a decrease in the behavior associated with social anxiety disorder, or a decrease in one or more behaviors associated with an obsessive compulsive disorder.

The treatment can be repeated when the partial or complete muscle paralysis induced by the agent begins to abate. Alternatively, one can also wait for any signs or symptoms of the social anxiety disorder, the obsessive compulsive disorder or the panic disorder to also recur after the muscular activity returns.

An exemplary injection technique involves the use of a short, narrow needle (e.g. ½ inch or 8 mm; 30-gauge) with an insulin- or tuberculin-type syringe. Subjects are typically treated in the seated position. The skin area is cleaned with an alcohol swab. A single syringe may be used for multiple injections to treat different locations in a single muscle or more than one muscle. Typically, the plunger of the syringe is depressed as the needle is withdrawn so that toxin is evenly distributed at the injection site. Pressure or gentle massage may be applied at the injection site to assist in dissipating the toxin. The toxin will typically migrate approximately 1 cm from the site of injection. Without being bound by theory, the toxin (such as BTX A) does not cross the blood brain barrier.

Electromyographic (EMG) guided needles may be used for injection to determine needle location of a high degree of accuracy, although this technique is generally not necessary.

For applications of BTX, such as BTX A, total dose per treatment can be varied and depends upon the condition being treated and the site of application of BTX. For example, a total dose of about 10 to about 60 Unit equivalents, such as about 20 to about 50 Unit equivalents, about 30 to about 60 Unit equivalents, about 29 to about 40 Unit equivalents, or about 20 to about 40 Unit equivalents. The BTX, such as BTX A, will typically be applied to corrugator supercilii and the procerus muscle (see, Carruthers and Carruthers, *Dermatol. Surg.* 24:1168-1170, 1998 for dosing information). In any of these dosages, the administration can be repeated. In some embodiments, BTX, such as BTX A, is not administered to the orbicularis oculi, frontalis, and/or the depressor anguli oris muscles (triangularis muscle). In one specific non-limiting example, about 20 to about 50 Unit equivalents of BTX A is administered only to the corrugator supercilii and/or the procerus muscle or both. In one non-limiting example, a total of about 29 units of BTX A is administered to the corrugator supercilii and the procerus muscle.

In further embodiments, a total dose of about 30 to about 60 Unit equivalent of BTX are administered to the corrugator supercilii, procerus muscle and the depressor angularis oris muscle.

In some non-limiting examples, a total of about 28 to about 58 Unit equivalents of BTX are administered to the corrugator supercilii, procerus muscle, and depressor angularis oris muscles, wherein about 4 Unit equivalents are administered to the left depressor angularis oris muscle and to the right depressor angularis oris muscle.

Onset of muscle paralysis following injection usually occurs within days of treatment, although it can take up to ten days for full paralysis to occur. In some embodiments, it can take one or two days for relief of symptoms, but it may take longer, such as a week or two weeks for improvement. The duration of paralysis will vary from patient to patient. Typically, duration will be from two to eight months, for example about three to about six months, or for example about three months, before subsequent treatment is required to alleviate the condition, although BTX can have an efficacy for up to 12 months (Naumann et al., *European J. Neurology* 6(Supp 4):S111-S115, 1999).

Administration of the BTX can be repeated. In some embodiments, the BTX can be repeated at about two to about six month intervals, such as at about two, three, four, five, six, seven or eight month intervals. In other embodiments, administration is provided over a period of about about six months, or for about one, about two, about three, about four or about five years. Thus, in some non-limiting examples, BTX is administered every two to eight months for a period of one, two, three, four or five years.

Thus, in one specific, non-limiting example, to treat the social anxiety disorder, the obsessive compulsive disorder or the panic disorder, the corrugator supercilii and/or the procerus muscle is treated repeatedly. For example, about 30 to about 60 Unit equivalents of BTX A, such as about 20 to about 40 Unit equivalents, about 30 to about 40 Unit equivalents of BTX A, or about 29 Unit equivalents, is administered to the corrugator supercilii and/or the procerus muscle. After a period of about three months, and additional about 30 to about 60 Unit equivalents, such as about 20 to about 40 Unit equivalents, about 30 to about 40 Unit equivalents, or about 29 Unit equivalents of BTX A is administered to the corrugator supercilii and/or procerus muscle. This treatment can be administered as many times as needed to alleviate the social anxiety disorder, the obsessive compulsive disorder or the panic disorder. Another neurotoxin can be used similarly, such as another BTX.

Figure 2A:
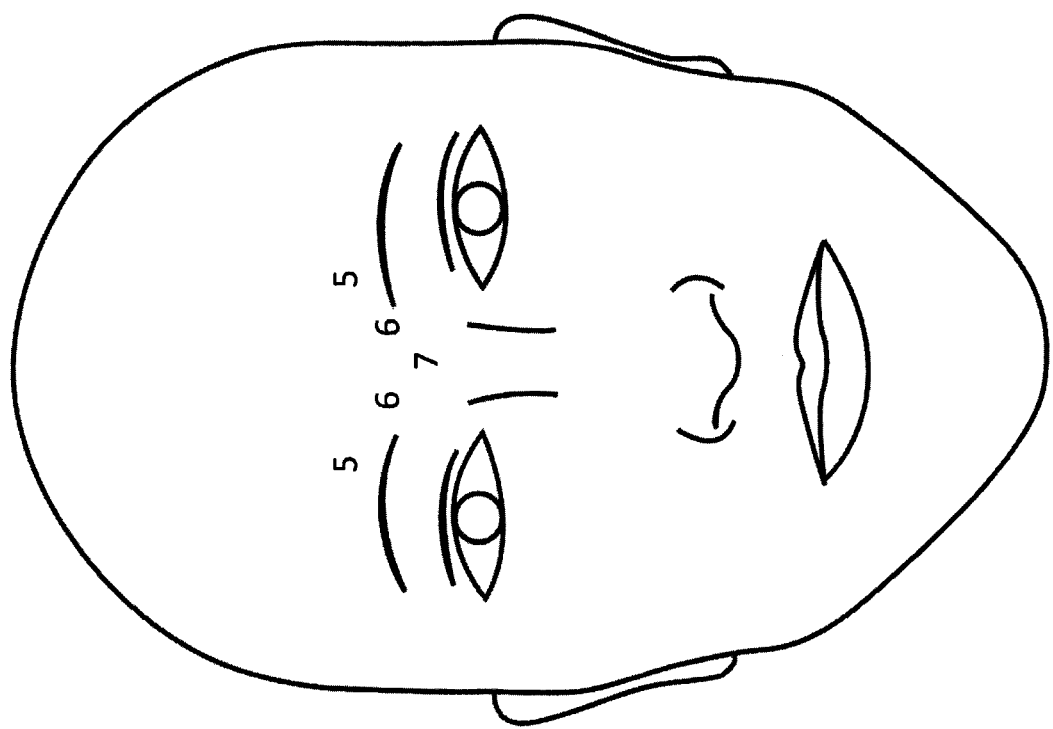
FIGS. 2A-2B show Botulinum toxin dose used to treat the frown in a typical woman (FIG. 2A) and man (FIG. 2B). The landmarks for the injection are as follows (see also Carruthers et al., *Derm. Surg.* 24:1189-1194, 1998). The injection of the procerus is below a line joining the medial end of both eyebrows. The landmark for the next injections is a line vertically above the inner canthus and the superior margin of the orbit. Botulinum toxin is injected just superior to the first injection point. Next an injection is made 1 centimeter (cm) medial and one-half cm superior to the second two injections. The numbers refer to the number of BTX Units injected in the area shown.
Figure 2B:
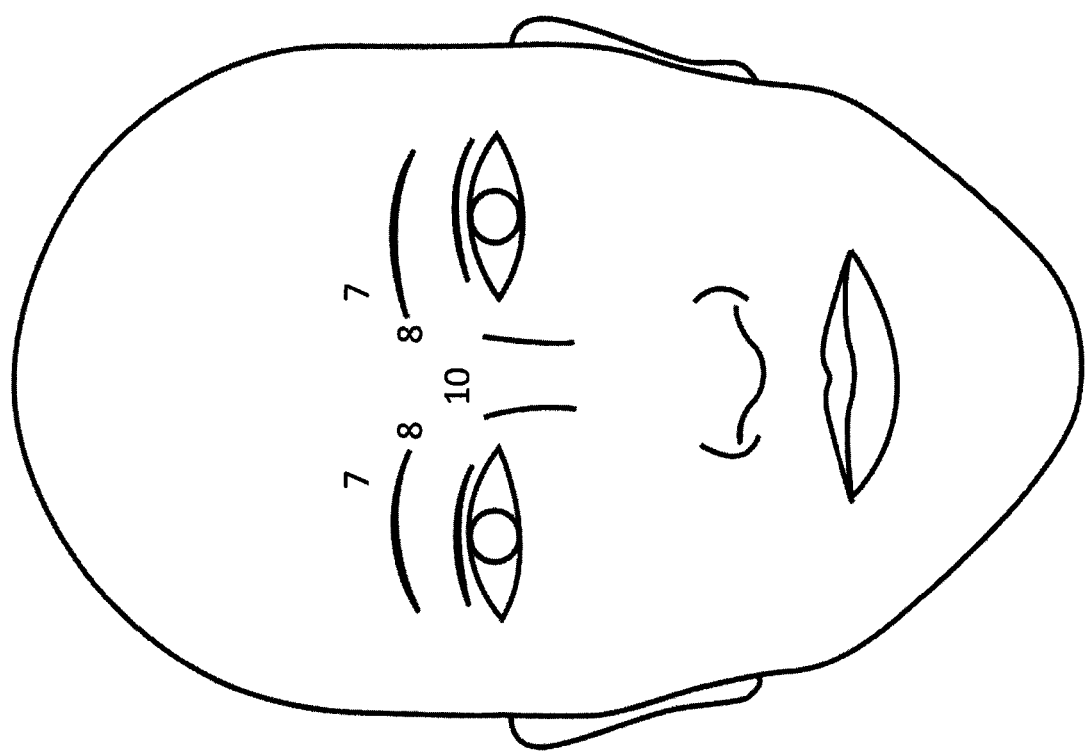

FIGS. 2A-2B show Botulinum toxin dose used to treat the frown in a typical woman (FIG. 2A) and man (FIG. 2B). The landmarks for the injection are as follows (see also Carruthers et al., *Derm. Surg.* 24:1189-1194, 1998). The injection of the procerus is below a line joining the medial end of both eyebrows. The landmark for the next injections is a line vertically above the inner canthus and the superior margin of the orbit. Botulinum toxin is injected just superior to the first injection point. Next an injection is made 1 centimeter (cm) medial and one-half cm superior to the second two injections. The numbers refer to the number of BTX Units injected in the area shown.

EXAMPLES

Example 1

Case Study 1

S.W. is a 30 year old Caucasian female with a long history of anxiety induced by group social settings. She had been diagnosed with social anxiety disorder. On physical exam she was noted to have hyperexpressive facial movements. When the use of botulinum toxin to treat her social difficulties was discussed, her brow and mouth underwent rapid cycling between extreme displeasure and neutral expression. During the course of a 5 minute conversation, her frown musculature was observed to quickly and visibly contract no less than twenty times. However, her at rest expression was neutral.

She stated that she worked for a large biomedical firm in an administrative capacity. She found the group meetings, with many staffers, including some relative strangers, to be extremely stressful, both before and during, with anticipatory anxiety. S.W. complained that other members of the group would shy away from her; she thought that that might be because her face was so expressive. She would get very anxious during a meeting with her colleagues, and believed that her anxiety was easily observed by her colleagues around the room. She was sure that her face would tell others what she was feeling about them at that moment. Consequently, she felt that her innermost thoughts could be observed by all in the room, causing her tremendous anxiety. She saw others recoil away from her and was absolutely convinced it was from a facial expression she had just made. Consequently, she would try and avoid close one on one interactions with her colleagues. This severely impeded her ability to work in any group setting, and completely prevented her from advancing in the organization.

S.W. was treated with 29 units of botulinum toxin A to her frown (corrugator supercilii muscle and procerus muscle). She was seen back in follow up 6 and 12 weeks later. She was unable to voluntarily make a frown and did not contract her frown muscles during the office visit. She reported that her anxiety before and during meeting, was markedly reduced. She no longer dreaded meeting with colleagues. She was convinced that she no longer displayed to others her displeasure or disagreement with them. Consequently, she was now able to successfully negotiate her daily meetings with fellow staffers without undue apprehension or anxiety. She stated that other staffers no longer shied away from her. Her fear of interacting with colleagues had so diminished that she would no longer suffer anxiety before or during her meetings, allowing her to feel that she could contribute as well as any of the others.

Example 2

Case Study 2

R.D. is a 22 year old college student who experienced her first panic attack at 17. She had been raped by a high school acquaintance when she was 14. She did not inform her parents about the incident at the time. Shortly thereafter she began to suffer from bouts of bulimia and intermittent depression. She was prescribed Escitalopram, 20 mg orally per day, and her depression improved.

However, while on Escitalopram she began to suffer from panic attacks, which consisted of heart pounding, headaches, tachycardia, sweating, shortness of breath and an impending sense of doom. Sometimes the attacks would be triggered by academic deadlines; most often they were triggered by anxiety centered around her relationships with others. She was in ongoing psychotherapy, which gradually helped with the bulimia but the panic attacks continued.

She began studying at an elite university. A stressful roommate interaction her freshman year triggered another bout of depression. She underwent intensive psychotherapy, and her depression remitted. However, her panic attacks persisted. They occurred on average, once every few weeks. Although they would generally spontaneously resolve within a couple of hours, on one occasion they almost led to an emergency room visit. Although she knew it unlikely, she felt like she was having a heart attack. The panic attacks would interfere with her ability to read and/or prepare for exams. She could not focus for prolonged periods after the start of a panic attack. She felt paralyzed mentally for many hours after an attack. She also worried that they would occur at a really inopportune time. They would also cause her to think negatively about all her studies and her future ability to handle her academic studies.

At age 21 R.D. was treated with 29 units of botulinum toxin A to her frown muscles (corrugator supercilii muscle and procerus muscle). At follow up at 6 weeks she stated that she had not had another panic attack. She had two more treatments with botulinum toxin A. She remained panic attack free, nine months since the initial treatment with botulinum toxin A. She no longer experienced chest palpitations, heart pounding, sweating or tachycardia. Her view of the future also became more positive. She no longer worried whether or not she might have a panic attack in the middle of a really important academic time. She became more sure of her ability to handle her difficult academic work. When asked about the rape, she stated that she no longer thinks about it much.

Example 3

Case Study 3

A.R. is a 28 year old Caucasian female with a history of severe social anxiety disorder that had been diagnosed in college. She took no medications. Her brother also suffered from social anxiety disorder, and had become a drug addict. She was an excellent student and went on to receive a masters in chemical engineering. She was currently employed at a large chemical company in Virginia.

She was extremely attractive but could not recall the last time that she had dated. She stated that going out on dates caused too much anxiety. Any group interaction with strangers also caused her undue anxiety. In particular, she experienced extreme emotional difficulty with group office meetings. Unfortunately this was a common occurrence in her current work. Just prior to, and during any office meeting with coworkers, emotions of fear and anxiety would flood her mind, to the extent that she could not focus during the meeting. She complained of how her fear of group meetings completely prevented her from advancing in the company, and made her time there very stressful.

Although she had many ideas to contribute, any group meeting would prevent her from speaking up. She was incapable of any open disagreement with colleagues, or giving a presentation to the group, in spite of her desire to do so.

She received 29 units of botulinum toxin A to her frown muscles (corrugator supercilii muscle and procerus muscle). At her 6 week follow up she stated that her anxiety in her workplace had greatly diminished; she was now able to speak up at office meetings without anxiety. She stopped viewing her work as very stressful. At her three month follow up she spontaneously related that she had had three dates in the past two weeks—more than she had had in the past two years. She no longer trembled at the thought of dating a stranger. Her social anxieties had greatly diminished and she felt in much better control of her life.

It will be apparent that the precise details of the methods or compositions described may be varied or modified without departing from the spirit of the described invention. We claim all such modifications and variations that fall within the scope and spirit of the claims below.

The invention claimed is:

1. A method for treating a panic disorder in a subject, comprising administering a therapeutically effective amount of a botulinum toxin to a facial muscle involved in frowning, scowling, or a sad appearance of the subject to cause paralysis of facial muscle involved in frowning, scowling, or a sad appearance of the subject or a panic disorder in a subject, thereby treating the panic disorder in the subject.

2. The method of claim 1, wherein the Botulinum toxin is Botulinum toxin A.

3. The method of claim 2, wherein the subject does not have any other psychiatric disorder.

4. The method of claim 2, wherein the subject does not have a muscular disorder or paralysis.

5. The method of claim 2, wherein about 20 to about 50 Unit equivalents of Botulinum toxin type A are administered to the corrugator supercilii and the procerus muscle in the subject.

6. The method of claim 5, further comprising administering an additional dose of about 20 to about 50 Unit equivalents of Botulinum toxin type A to the corrugator supercilii and the procerus muscle after about two to six months.

7. The method of claim 3, wherein the subject is human.

8. The method of claim 1, further comprising administering to the subject a therapeutically effective amount of an additional modality of treatment for the panic disorder.

9. The method of claim 8, wherein the additional modality of treatment comprises an antidepressant, psychotherapy, or behavioral therapy.

10. The method of claim 8, wherein the additional modality of treatment comprises a selective serotonin reuptake inhibitor (SSRI), a tricyclic antidepressant, a benzodiazepine or an atypical antipsychotic.

* * * * *